United States Patent [19]

Dubus

[11] Patent Number: 4,847,495
[45] Date of Patent: Jul. 11, 1989

[54] METHOD OF QUANTITATIVE ANALYSIS BY MEANS OF THE MEAN ATOMIC NUMBER OF PHASES CONTAINING A LIGHT ELEMENT USING A SCANNING MICROSCOPE AND AN IMAGE ANALYSER

[75] Inventor: Alain Dubus, Coublevie, France
[73] Assignee: Pechiney, Paris, France
[21] Appl. No.: 169,601
[22] Filed: Mar. 17, 1988
[30] Foreign Application Priority Data
Apr. 13, 1987 [FR] France ................. 87 05562
[51] Int. Cl.$^4$ .......................... G01N 23/225
[52] U.S. Cl. ..................... 250/307; 250/310
[58] Field of Search ............... 250/307, 306, 310, 397

[56] References Cited

U.S. PATENT DOCUMENTS

| | | | |
|---|---|---|---|
| 4,236,178 | 11/1980 | Tiemeijer | 358/93 |
| 4,559,450 | 12/1985 | Robinson et al. | 250/310 |
| 4,697,080 | 9/1987 | King | 250/307 |

OTHER PUBLICATIONS

"Backscattered Electrons as an Analytical Technique", R. E. Ogilve, Fourth Symposium on Electron Beam Technology, Mar. 1962.
M. D. Ball et al., Journal of Microscopy, vol. 124, Pt. 1, Oct. 1981, pp. 57-68.

*Primary Examiner*—Jack I. Berman
*Attorney, Agent, or Firm*—Dennison, Meserole, Pollack & Scheiner

[57] ABSTRACT

The invention relates to an accurate method of quantitative analysis by the quantitative determination of the mean atomic number of phases containing two light elements or one light element combined with heavy elements using a scanning microscope connected to an image analyser of the intensity of the back-scattered electrons. This method of quantitative analysis by the quantitative determination of the mean atomic number ($\overline{Z}_1$) with a precision of $\pm 0.1$ unit of an unknown phase present in the plane micrographic section of a sample, containing either two light elements ($3 \leq Z \leq 11$) or at least one heavy element ($Z > 12$) and a single light element ($3 \leq Z \leq 11$) using a scanning electron microscope comprising analyser X coupled to an image analyser, the image analyser allowing the local intensity of the back-scattered electrons to be measured by the level of greyness (G) of the corresponding image, this method involving, under given operation conditions:

(a) determination of the calibration curve $G = f(\overline{Z})$ by means of a known samples,
(b) determination of the level of greyness ($G_1$) of the unknown phase under consideration,
(c) determination of ($\overline{Z}_1$) by the equation given in a),
(d) determination of the chemical composition by means of the equation $\overline{Z}_1 - g(n_1, Z_i)$, $n_1$ being the atomic abundance of the element of atomic under $Z_i$ present in the phase under consideration, and wherein the values of G or of $G_1$ are determined by the arithmetic mean of the levels of greyness measured by the image analyser over the entire surface of the unknown phase or phases and/or of the reference sample or samples present in the visualized field. This method can be used for the identification of a very large number of phases such as carbides, nitrides, borides, oxides, etc.

2 Claims, 1 Drawing Sheet

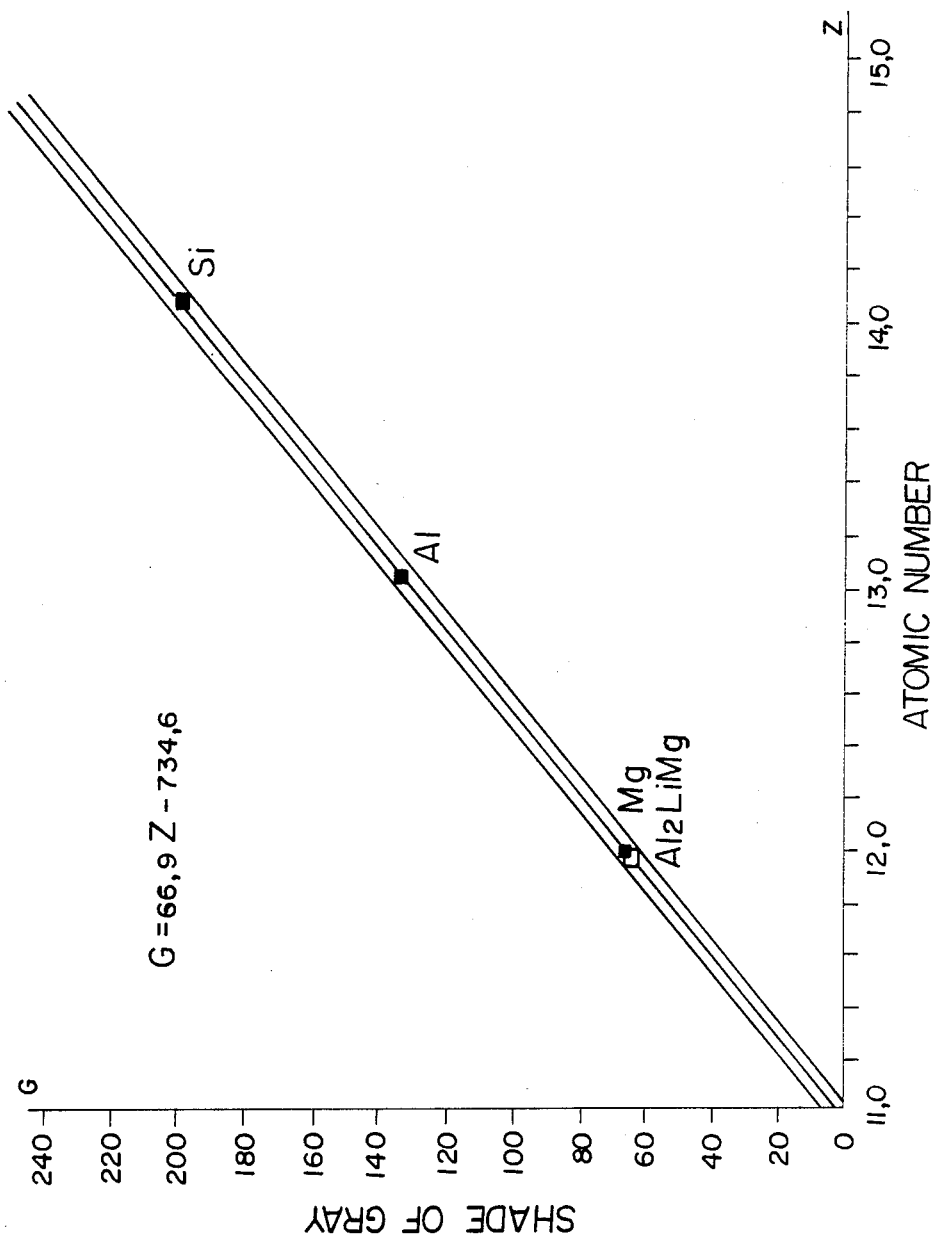

METHOD OF QUANTITATIVE ANALYSIS BY MEANS OF THE MEAN ATOMIC NUMBER OF PHASES CONTAINING A LIGHT ELEMENT USING A SCANNING MICROSCOPE AND AN IMAGE ANALYSER

The invention relates to a method of accurate quantitative analysis by the quantitative determination of the mean atomic number of phases containing two light elements or a light element combined with heavy elements using a scanning microscope connected to an image analyser of the intensity of the back-scattered electrons.

It is known that the intensity of back-scattered electrons is an increasing function of the mean atomic number ($\overline{Z}$) of the target. This phenomenon is exploited for obtaining a so-called "electronic" image of the sample in which the contrast is due to the variation of $\overline{Z}$ in the phases encountered.

Quantitative measurement of the mean atomic number and consequently of the composition of phases present at the surface of samples having at least one plane portion by means of the intensity of the back-scattered electrons (BSI in English) in scanning microscopy is known from numerous publications. We will mention, for example: M. D. BALL and D. G. McCARTNEY, Journal of Microscopy Volume 124, Pt. 1, October 1981, Pages 57-68 (1) or N. J. OWEN et al, The Institute of Metals Al-Li alloys III—Oxford—July 8-11, 1985, Pages 576 to 583 (2).

However, two problems arise when determining this atomic number:

in spite of all the precautions taken, the measurement is imprecise, particularly for low mean atomic numbers ($\overline{Z} < 11$) where it is of the order of $\pm 0.5$ unit ((2)—page 578); this does not allow a distinction from the phases of adjacent compositions;

the spatial resolution, that is to say the volume of the sample from which the back-scattered electrons originate, is generally limited to a few $\mu m$, either in depth (2.5 $\mu m$ in Al according to (1), page 60), or in diameter (1 $\mu m$ in Al according to (1), page 62).

It is consequently difficult to determine the atomic number of phases having small dimensions (for example $<1$ $\mu m$ in section) owing to the contribution to the analysed signal of that due to the matrix adjacent to the analysed phases.

The method according to the invention overcomes these two drawbacks.

According to the invention, the method of quantitative determination of the mean atomic number ($\overline{Z}_1$) with an accuracy of $\pm 0.1$ unit of an unknown phase present in the plane micrographic section of a sample containing either two light elements ($3 \leq Z \leq 11$), or at least one heavy element ($Z \geq 12$) and a single light element ($3 \leq Z \leq 11$) using a scanning electron microscope comprising an analyser X coupled to an image analyser, the image analyser allowing the local intensity of the back-scattered electrons to be measured by the level of greyness (G) of the corresponding image, this method involving, under the given operating conditions:

(a) determination of the calibration curve $G = f(\overline{Z})$ by means of known samples, (b) determination of the level of greyness ($G_1$) of the unknown phase under consideration, (c) determination of ($\overline{Z}_1$) by the equation given in (a), (d) determination of the chemical composition by means of the equation $\overline{Z}_1 = g(n_i, Z_i)$, $n_i$ being the atomic abundance of the element having atomic number $Z_i$ present in the phase under consideration, characterised in that the values of G or of $G_1$ are determined by the arithmetic mean of the levels of greyness measured by the image analyser over the entire surface of the unknown phase or phases and/or over the reference sample or samples present in the visualized field.

Spatial resolution is improved and reaches 0.5 $\mu m^3$ and even 0.1 $\mu m^3$ over the heavy matrices when the acceleration voltage of the scanning microscope is limited to 10 kV, preferably 5 kV.

BRIEF DESCRIPTION OF THE DRAWING

The invention will be understood better by means of the following example and FIG. 1 showing the calibration curve $G = f(\overline{Z})$.

EXAMPLE 1

Determination of the nature of a Al-Li-Mg phase

The apparatus used is constituted by a DSM 950 type Zeiss scanning microscope connected to a SEM-IES type Kronton image analyser with suitable interface.

The measurements were taken under the following conditions on three pure samples (Mg, Al, Si) and on the unknown phase containing Al-Mg-Li, present in a sample of alloy in which the unknown phase represents about 25% by volume of the sample under consideration and is distributed in the form of isolated phases, the size of which ranges from 10 to 30 $\mu m$.

Scanning microscope:

| | |
|---|---|
| Acceleration voltage | 25 kV |
| Beam current | 400 pA |
| Operating distance | 9 mm |
| Diaphragm | 400 $\mu m$ |
| Magnification | $\times$ 300 |

Image analyser:

Adjustment of the amplification and the threshold so that the level of greyness $G = 0$ (black) corresponds to $Z = 11$ and the level of greyness $G = 255$ (white) corresponds to $Z = 15$. Acquisition of the image of $256 \times 256$ points covering an effective surface area of 300 $\mu m^2$ on the sample. Preferably presence of several phases of the same nature on the same image.

Under these conditions, the time for acquisition of an image is about 20 sec.

The results obtained are as follows:

| Element | Z | Number of Measurements | Level of Greyness G | Confidence Interval at the risk of 5% |
|---|---|---|---|---|
| Mg | 12 | 7 | 68.4 | +−5.3 |
| Al | 13 | 5 | 136.6 | +−2.5 |
| Si | 14 | 7 | 202.3 | +−2.0 |

It can be deduced from this that the calibration curve is a straight line having the equation:

$$G = 66.9Z - 734.6$$

(See FIG. 1)

with a coefficient of correlation $r = 0.99994$.

The measurement of G over the phase (Al-Li-Mg) is:

$69.5 \pm 4.3$ at a risk of 5% (6 measurements).

It has also been determined by a known method, using the analyser X of the scanning microscope, that the atomic ratio Al/Mg is 2/1. The formula of the unknown phase is therefore $Al_2MgLi_x$.

The mean atomic number $\overline{Z}$ is connected to the atomic number of the elements present ($Z_i$) and their atomic abundance ($n_i$) by the experimental formula $$\overline{Z} = (\Sigma n_i Z_i^2)/(\Sigma n_i Z_i)$$

according to L. DANDY and R. QUIVY, J. Phys. Radium. 6, 320 (1956).

It can be deduced that:

$$\overline{Z} = (69.5 + 734.6)/(66.9)32$$
$$12.02 = (2 \times 13^2 + 12^2 + 3^2 x)/(2 \times 13 + 12 + 3x)$$

that is $x = 0.933 \simeq 1$.

The unknown phase is therefore the compound defined as $Al_2LiMg$.

EXAMPLE 2

Stoichiometry of SiC in a thin deposit ($e \neq 1$ μm)

The operating, sampling and calculation conditions are the same as in Example 1.

The presence of a single heavy element produces a direct relationship between the atomic number measured and the index x in the formula $SiC_x$.

The measurement of G in the phase $SiC_x$ is $47.0 \pm 4.4$ at the risk of 5% (6 measurements).

A mean atomic number of 11.7 is deduced from it, leading to $x = 0.94 \pm 0.06$. The compound is not therefore significantly different from the stoichiometric phase.

Apart from its high accuracy and its high spatial resolution, this method affords the following advantages:

speed of acquisition and of processing of the images,
cleaning of the images with suitable filters,
possibility of eliminating possible defects (scratches, dust, etc).

This method can be used for identification a very large number of phases such as carbides, nitrides, borides, oxides, etc.

I claim:

1. A method of quantitative analysis by a quantitative determination of the mean atomic number $\overline{Z}_1$ with an accuracy of $\pm 0.1$ unit of an unknown phase present in a plane micrographic section of a sample, containing either two light elements with mean atomic numbers equal to or no less than 3 or equal to or no greater than 11 or at least one heavy element with a mean atomic number equal to or greater than 12 and a single light element with mean atomic numbers equal to or no less than 3 or equal to or no greater than 11 using a scanning electron microscope coupled to an image analyser, the image analyser allowing the local intensity of the back-scattered electrons to be measured by a level of greyness G of a corresponding image, comprising:

(a) determination of a calibration curve $G = f(\overline{Z})$ by means of known samples wherein G indicates the level of greyness measured by said image analyser and $\overline{Z}$ indicates the mean atomic member of said known samples, (b) determination of the level of greyness ($G_1$) of the unknown phase under consideration, (c) determination of ($\overline{Z}_1$) by the equation given in, (a) wherein $\overline{Z}1$ indicates the mean atomic number of said unknown phase, and (d) determination of a chemical composition by means of an equation $\overline{Z}_1 = g(n_1, Z_i)$, $n_i$ being the atomic abundance of the element of atomic number $Z_i$ present in the phase under consideration, wherein the values of G or of $G_1$ are determined by the arithmetic mean of the levels of greyness measured by the image analyser over the entire surface of the unknown phase or phases and/or of the reference sample or samples present in a visualized field.

2. The method according to claim 1, allowing a spatial resolution of up to 0.1 μm³ to be achieved, wherein the acceleration voltage of the scanning electron microscope is less than 10 kv.

* * * * *